(12) United States Patent
Xu et al.

(10) Patent No.: US 9,683,314 B2
(45) Date of Patent: Jun. 20, 2017

(54) OXYGEN AND NITROGEN CO-DOPED POLYACRYLONITRILE-BASED CARBON FIBER AND PREPARATION METHOD THEREOF

(71) Applicant: Ocean University of China, Qingdao, Shandong Province (CN)

(72) Inventors: Haibo Xu, Qingdao (CN); Yonghong Lu, Qingdao (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 0 days.

(21) Appl. No.: 14/765,826

(22) PCT Filed: Feb. 19, 2013

(86) PCT No.: PCT/CN2013/071657
§ 371 (c)(1),
(2) Date: Aug. 4, 2015

(87) PCT Pub. No.: WO2014/127501
PCT Pub. Date: Aug. 28, 2014

(65) Prior Publication Data
US 2015/0376817 A1    Dec. 31, 2015

(51) Int. Cl.
*D01F 11/16* (2006.01)
*D01F 11/12* (2006.01)
(Continued)

(52) U.S. Cl.
CPC ............ *D01F 11/16* (2013.01); *C07D 471/22* (2013.01); *D01F 11/129* (2013.01); *H01M 4/96* (2013.01);
(Continued)

(58) Field of Classification Search
CPC ... D01F 9/21; D01F 9/22; D01F 11/10; C01B 31/0273; C07D 471/122; D10B 2101/12; D10B 2321/10
See application file for complete search history.

(56) References Cited

U.S. PATENT DOCUMENTS 4,704,196 A * 11/1987 Saito ............... C25D 11/34
204/DIG. 8

FOREIGN PATENT DOCUMENTS

CN    101066802    11/2007
CN    101660185    3/2010
(Continued)

OTHER PUBLICATIONS

Removal of NO using surface modified activated carbon fiber (ACF) by impregnation and heat-treatment of propellant waste Korean Journal of Chemical Engineering (2010), 27(6), 1882-1886 CODEN: KJCHE6; ISSN: 0256-1115; English.*
(Continued)

*Primary Examiner* — Richard M Rump
(74) *Attorney, Agent, or Firm* — Loza & Loza, LLP; Michael F. Fedrick

(57) ABSTRACT

The invention relates to an oxygen and nitrogen co-doped polyacrylonitrile-based carbon fiber and a preparation method thereof. The oxygen and nitrogen co-doped polyacrylonitrile-based carbon fiber is prepared by electrochemical modification of a raw-material polyacrylonitrile-based carbon fiber, such that the surface thereof has an active layer formed by oxygen-containing active functional groups and nitrogen-containing active functional groups, wherein the nitrogen-containing active functional groups are obtained by activation of the doped nitrogen inherently contained in the raw-material polyacrylonitrile-based carbon fiber by means of electrochemical modification. The method for preparing the oxygen and nitrogen co-doped polyacrylonitrile-based
(Continued)

carbon fiber comprises the following steps: placing the raw-material polyacrylonitrile-based carbon fiber in an electrolyte solution, subjecting it to cyclic treatment between electrochemical oxidation and electrochemical reduction, and thus obtaining the oxygen and nitrogen co-doped polyacrylonitrile-based carbon fiber. The oxygen and nitrogen co doped polyacrylonitrile based carbon fiber of the present invention has both the pseudo capacitive properties for oxidation reduction reactions and electrocatalytic properties for the cathodic oxygen reduction reaction.

14 Claims, 5 Drawing Sheets

(51) Int. Cl.
    *C07D 471/22*     (2006.01)
    *H01M 4/96*     (2006.01)
    *H01M 6/34*     (2006.01)
    *H01M 12/06*     (2006.01)

(52) U.S. Cl.
    CPC ............ *H01M 6/34* (2013.01); *H01M 12/06* (2013.01); *D10B 2101/12* (2013.01); *D10B 2321/10* (2013.01)

(56) References Cited

FOREIGN PATENT DOCUMENTS

| | | | |
|---|---|---|---|
| CN | 101697323 | | 4/2010 |
| CN | 101718011 | | 6/2010 |
| CN | 102176380 | | 9/2011 |
| CN | 101718011 B | * | 11/2011 |
| EP | 2543631 | | 1/2013 |
| JP | 1986282470 | | 12/1986 |
| JP | 02104767 A | | 4/1990 |
| JP | 1990169763 | | 6/1990 |
| JP | 2006183173 A | * | 7/2006 |
| JP | 2006183173 A | | 7/2006 |
| JP | 2012102439 | | 5/2012 |
| JP | 2012102439 A | * | 5/2012 |

OTHER PUBLICATIONS

Xue, Yan, Jie Liu, and Jieying Liang. "Correlative study of critical reactions in polyacrylonitrile based carbon fiber precursors during thermal-oxidative stabilization." Polymer Degradation and Stability 98.1 (2013): 219-229.*
Abdelkareem, Mohammad Ali, et al. "PAN Based Carbon Nanofibers as an Active ORR Catalyst." Key Engineering Materials. vol. 497. 2012.*
Bayramli, Erdal, Levent Toppare, and Naci Kutay Erinc. "Investigations on the electrochemical surface treatment of carbon fibers." Turkish Journal of Chemistry 25.3 (2001): 251-258.*
Ma, Y. J., J. L. Wang, and X. P. Cai. "The effect of electrolyte on surface composite and microstructure of carbon fiber by electrochemical treatment." Int. J. Electrochem. Sci 8.2 (2013).*
Machine English translation of JP2006183173A.*
Machine English translation of 2012102439A.*
English machine translation of JP2006-169463A.*
Yuehua Wen, et al., Studies on Nitrogen-Doped Nano-Carbons and Their Non-Pt Metal Composites as Electrocatalysts, Progress in Chemistry, vol. 22, No. 8 1550-1555 (2010).
Hai-bo Xu, et al., Dissolved Oxygen Seawater Battery with Electrochemical Capacitance, Journal of Electrochemistry, vol. 18, No. 1, 24-30 (2012).
Gong K, et al., Nitrogen-Doped Carbon Nanotube Arrays with High Electrocatalytic Activity for Oxygen Reduction, Science, 2009, 323: 760-764.
Extended European Search Report issued on Sep. 12, 2016 for counterpart European Patent Application No. 13876075.6.
First Office Action issued for corresponding Japanese Patent Application No. 2015-557313 mailed on Oct. 18, 2016.
Y J Ma, et al., "The Effect of Electrolyte on Surface Composite and Microstructure of Carbon Fiber by Electrochemical Treatment", Int. J. Electrochem. Sci. International Journal, Feb. 1, 2013, vol. 8, pp. 2806-2815.
Ra, EJ, et al., "High power supercapacitors using polyacrylonitrile-based carbon nanofiber paper", CARBON, vol. 47, No. 13, Nov. 1, 2009, pp. 2984-2992.
Abdelkareem, MA, et al., "PAN Based Carbon Nanofibers as an Active Orrcatalyst", Key Engineering Materials, vol. 497, Dec. 1, 2011, pp. 73-79.

* cited by examiner

OXYGEN AND NITROGEN CO-DOPED POLYACRYLONITRILE-BASED CARBON FIBER AND PREPARATION METHOD THEREOF

CROSS-REFERENCE TO RELATED APPLICATIONS

This application is the U.S. national stage of International Patent Application No. PCT/CN2013/071657, filed on Feb. 19, 2013 and entitled OXYGEN AND NITROGEN CO-DOPED POLYACRYLONITRILE-BASED CARBON FIBER AND PREPARATION METHOD THEREOF, the disclosure of which is incorporated herein by reference in its entirety.

TECHNICAL FIELD

The present invention relates to oxygen and nitrogen co-doped polyacrylonitrile-based carbon fibers and the preparation method thereof, and in particular, to oxygen and nitrogen co-doped polyacrylonitrile-based carbon fibers prepared by electrochemical modification. The present invention belongs in the technical field of electrochemistry of materials.

BACKGROUND ART

Carbon fibers are obtained from carbonization or graphitization of organic fibers and have turbostratic graphitic microstructure. They are inorganic high-molecular-weight fibers having a carbon content above 90%, and are called graphite fibers when the carbon content is higher than 99%. Carbon fibers have high axial strength and modulus, no creep, good fatigue resistance and corrosion resistance, specific heat and conductivity between those of non-metal and metal, a small thermal expansion coefficient, low fiber density and good X-ray transmission, while they are poor in impact resistance, prone to damage, and oxidized under the action of strong acids, and may also lead to phenomena like metal carbonization, carburization and electrochemical corrosion when compounded with metals. Therefore, surface treatment of carbon fibers before use is necessary.

Carbon fibers can be prepared from carbonization of each of polyacrylonitrile fibers, pitch fibers, viscose or phenolic fibers, and can be classified into filaments, staple fibers and chopped fibers according to their state, or into general carbon fibers and high-performance carbon fibers according to their mechanical properties. General carbon fibers have strength of 1,000 MPa and a modulus of approximately 100 GPa. High-performance carbon fibers can be further categorized into the high-strength type (strength: 2,000 MPa; modulus: 250 GPa) and the high-modulus type (modulus: 300 GPa or higher), wherein those having strength higher than 4,000 MPa are called the ultrahigh-strength type and those having a modulus higher than 450 GPa are called the ultrahigh-modulus type. With the advances in the aeronautic and astronautic industry, a high-strength-and-high-elongation type of carbon fibers having elongation greater than 2% has also been developed. Polyacrylonitrile (PAN) carbon fibers are most used and have a market share of 90% or more. Preparation of carbon fibers comprises the following four procedures: fiber spinning (production of precursor), thermal stabilization (pre-oxidation), carbonization, and graphitization, during which the accompanying chemical reactions include dehydrogenation, cyclization, pre-oxidation, oxidation, deoxygenation, and the like.

PAN as the precursor of carbon fibers contains cyano groups (—C≡N), which have a high polarity and impart unique characteristics to the structure and performance of PAN. After sufficient carbonization (at 1,000° C. to 1,500° C.) of the PAN precursor, the mass percentages of N, H and O dramatically decrease and the carbon content reaches 93%-98%, while some doped nitrogen still remains with a nitrogen content of 2%-7%. Graphite fibers are obtained from high-temperature graphitization of carbon fibers at 2,200° C. to 3,000° C., which is a continuation of solid-phase carbonization, driving nearly all non-carbon elements (mainly nitrogen) out of the carbon fibers and leaving graphite fibers having almost 100% carbon. Therefore, one important feature of the PAN-based carbon fibers not treated with the high-temperature graphitization is its distinctive nitrogen-doped structure. For pitch-based carbon fibers, the content of doped nitrogen is low, generally less than 1%, while viscose-based carbon fibers do not contain doped nitrogen.

Thanks to their excellent mechanical property, carbon fibers have been used mainly as reinforcing components in composite materials. Recently, because of their superior conductivity, for example the T700PAN-based carbon fibers produced by Toray Industries, Inc., Japan having resistivity of $1.6 \times 10^{-3}$ Ω·cm, carbon fibers have started drawing attentions for their application in electrochemistry, and may be used to produce electrode materials for cells utilizing oxygen dissolved in seawater (metal half-fuel cells using seawater as the medium), proton exchange membrane fuel cells, metal-air fuel cells, microbial fuel cells, a supercapacitor, redox flow cells, lead-acid cells, lithium-ion cells, electrochemical treatment of waste water, an electrochemical transducer, and the like.

Carbon fibers may serve as the electrode material for cathodic oxygen reduction. Oxygen reduction reaction (ORR) plays a vital role in electrochemistry. In various fuel cell technologies, electric powder is generated from an electrochemical reaction constituted by the cathodic oxygen reduction and the anodic oxidation of fuels (such as hydrogen, methanol, active metal, microorganisms, etc.). In the waste water treatment technology by the Electro-Fenton method, cathodic oxygen reduction by electrochemical means produces $H_2O_2$ as a continuous source of the Fenton reagent, and the $H_2O_2$ reacts with $Fe^{2+}$ in the solution to produce a highly oxidizing .OH free radical, which can nonselectively destroy nearly all organic contaminants to complete mineralization. Hence, development of carbon-fiber electrode material having excellent electrocatalytic activity for cathodic oxygen reduction offers very bright prospects for various applications.

Fuel cells have been well acknowledged as a clean energy-conversion system. However, their commercialization has been thwarted by two major technical limitations, i.e. cost and reliability. Currently, Pt-based catalysts are the major reason for the high cost of fuel cells, and cheap, highly active and highly stable electrocatalysts for oxygen reduction have been the hot spot of research on fuel cells. In recent years, the fact that nitrogen doping has a significant impact on the performance of carbon and its composite electrocatalyst has attracted wide attention. It has been reported that nitrogen-doped carbon and its composite material have significantly improved catalytic performance which in a basic medium surpasses that of commercial Pt catalysts, and look very promising as a non-noble metal catalyst to replace Pt for use in fuel cells (Gong K, et al., Nitrogen-Doped Carbon Nanotube Arrays with High Electrocatalytic Activity for Oxygen Reduction, Science, 2009. 333: 760-764).

Methods for doping nitrogen in carbon material can be basically classified into (1) in situ doping, wherein nitrogen is doped during synthesis of carbon material; and (2) post doping, wherein synthesized carbon material is subjected to post-treatment with a N-containing precursor (Wen Y, et al., Studies on Nitrogen-Doped Nano-Carbons and Their Non-Pt Metal Composites as Electrocatalysts, *Progress in Chemistry,* 2010, 22: 1550-1555). In in situ doping, chemical vapor deposition (CVD) is performed on a substrate or template with an organic nitride as a precursor, and, similar to hydrocarbons, the nitride may retain some C—N bonds when the substrate decomposes such that a N-doped nanostructure is formed. In post doping, nano-carbon undergoes post-treatment in a nitrogen-containing atmosphere, so as to afford nitrogen-doped nano-carbon material. Both doping methods are for nano-scale carbon material and generally require a preparation temperature not higher than 1,000° C. A preparation temperature over 1,000° C. may lead to severe escaping of doped nitrogen, which affects the nitrogen doping effect, while an excessively low preparation temperature may also create negative impacts on conductivity of the nitrogen-doped carbon material. In addition, the reactions during the preparation require strict conditions and thus are not suitable for large-scale production, and in actual applications an adhesive agent will be required to manufacture an electrode from the prepared nano-scale nitrogen-doped carbon material.

Commercialized PAN-based carbon fibers are fibrous structures in a size of a few microns, excellent in conductivity, and easy to be processed into an electrode. Commercialized SWB1200 seawater cells (Kongsberg Simrad, Norway), which employ a brush electrode made from PAN-based carbon fibers as the positive electrode for the seawater cells utilizing dissolved oxygen. Although obtained through carbonization at a temperature over 1,000° C., such commercialized PAN-based carbon fibers still have a residual doped nitrogen content of 2%-7%. Therefore, the doped nitrogen contained therein has higher thermal and chemical stability than those obtained by the two doping methods describe above. However, the doped nitrogen inherent in unmodified PAN-based carbon fibers has limited catalytic activity for ORR, and thus has not caught a lot of interest and needs certain modification to obtain good ORR activity (Xu H, et al., Seawater Battery with Electrochemical Supercapacitance, *Journal of Electrochemistry,* 2012, 18: 24-30).

Previous surface modifications of carbon fibers mainly aim to improve the binding strength between carbon fibers and the composite material, and major modification methods include ozone chemical oxidation and electrochemical anodic oxidation. PAN-based carbon fibers have a smooth surface and show chemical inertness, and these characteristics are unfavorable for them to produce good interface binding with a resin substrate. If surface treatment is applied to PAN-based carbon fibers to introduce active groups onto the surface and increase the surface roughness, then the binding of the carbon fibers can be improved and the mechanical performance of resin-based composite material can be enhanced. Among these methods, anodic oxidation is easy to control, can achieve even oxidation of every fiber, has great operational flexibility, is readily applicable to large-scale treatment, and can increase the interlayer shearing strength in carbon-fiber composite material to about 100 MPa by introducing active functional groups such as oxygen- and nitrogen-containing groups to the surface. However, anodic oxidation as a method for improving mechanical performance requires mild oxidation conditions. Furthermore, if anodic oxidation is used alone for treatment, the introduced oxygen-containing functional groups would be mostly located at the carbon basal planes, and the introduced nitrogen-containing functional groups would be an imino (—NH) or amino (—NH$_2$) group, in which case the introduced doped nitrogen comes from the compounds in the anodic oxidation solution and is not a nitrogen-containing functional group formed from the inherent doped nitrogen previously present in the carbon fibers. In addition, these oxygen- and nitrogen-containing functional groups fail to exhibit effective pseudocapacitive characteristics and electrocatalytic activity for cathodic oxygen reduction, and thus cannot meet the requirements on electrode material.

CN101697323A discloses an electrochemically modified graphite electrode, in which a graphite body is subjected to cyclic treatment between electrochemical oxidation and electrochemical reduction in an aqueous solution of an electrolyte, so as to directly obtain a rough, porous activated layer having certain thickness, abundant oxygen-containing active functional groups and a microcrystalline flake-like structure. The reversible redox reactivity of these oxygen-containing active functional groups may be used for an electrochemical capacitor. CN102176380A discloses a redox reaction electrochemical capacitor, and discloses that the electrochemically modified graphite electrode also has electrocatalytic activity for the redox couples frequently used in redox flow cells. Since graphite itself does not contain oxygen, the surface of the graphite electrode obtained after the above electrochemical treatment does not have a nitrogen-containing active functional group, and thus does not have the characteristics of nitrogen-doped material.

Furthermore, the electrochemical capacitor is characterized by high power, and the fuel cell is characterized by high energy density. Since they are individual devices, a combination thereof is needed to satisfy the requirement for both high power and high energy density with respect to power performance. If they are combined in one unit, the volume of the system will be reduced. This sets out a requirement for electrode material having the characteristics of both the electrochemical capacitor and the fuel cell (mainly depending on the ORR performance).

In summary, development of an oxygen and nitrogen co-doped PAN-based carbon fiber prepared by electrochemical modification remains a crucial problem to be eagerly solved in the field of electrochemistry of material.

SUMMARY OF INVENTION

In order to solve the above technical problems, the present invention aims to provide oxygen and nitrogen co-doped PAN-based carbon fibers which have on their surface oxygen-containing active functional groups and nitrogen-containing active functional groups, and also have pseudocapacitive characteristics for redox reactions and electrocatalytic activity for cathodic oxygen reduction reactions (ORR).

The present invention also aims to provide a method for preparing the oxygen and nitrogen co-doped PAN-based carbon fibers described above.

In order to achieve the above aims, the present invention provides a kind of oxygen and nitrogen co-doped PAN-based carbon fibers, which are prepared by electrochemical modification of raw-material PAN-based carbon fibers such that their surface has an active layer formed by oxygen-containing active functional groups and nitrogen-containing active functional groups, wherein the nitrogen-containing active functional groups are obtained after activation of the doped nitrogen inherent in the raw-material PAN-based carbon fibers by electrochemical modification. In the active layer, the oxygen-containing active functional groups have reversible redox reactivity, and the nitrogen-containing active functional groups have electrocatalytic activity for cathodic oxygen reduction. Therefore, the oxygen and nitrogen co-doped PAN-based carbon fibers according to the present invention have both the pseudocapacitive characteristics, generated on the basis of the reversible redox reactions of the active functional groups, and electrocatalytic activity for cathodic oxygen reduction.

In the oxygen and nitrogen co-doped PAN-based carbon fibers described above, preferably, the nitrogen-containing active functional groups are one or a combination of more of pyridinic nitrogen, pyrrolic nitrogen, graphitic nitrogen and the like located at the edges of carbon basal planes on the surface of the oxygen and nitrogen co-doped PAN-based carbon fibers. One or more of the nitrogen-containing active functional groups have electrocatalytic activity for cathodic oxygen reduction.

In the oxygen and nitrogen co-doped PAN-based carbon fibers described above, preferably, the oxygen-containing active functional groups are one or a combination of more of carboxyl oxygen, ketonic oxygen, hydroxyl oxygen and the like located at the edges of carbon basal planes on the surface of the oxygen and nitrogen co-doped PAN-based carbon fibers. The different oxygen-containing active functional groups have reversible redox reactivity therebetween.

In the oxygen and nitrogen co-doped PAN-based carbon fibers described above, preferably, the raw-material PAN-based carbon fibers have not been treated by graphitization, and have a nitrogen content of 1% or more with respect to the total mass of the raw-material PAN-based carbon fibers.

According to an embodiment of the present invention, preferably, the shape of the oxygen and nitrogen co-doped PAN-based carbon fibers described above may be one or a combination of more of the shapes of a bundle, felt, foam, a brush, paper, cloth, and the like. The oxygen and nitrogen co-doped PAN-based carbon fibers provided in the present invention may be obtained by electrochemical modification after being processed into the above shapes, or may be processed into the above shapes after electrochemical modification. A person skilled in the art can select a size for the PAN-based carbon fibers of different shapes upon needs.

In the oxygen and nitrogen co-doped PAN-based carbon fibers described above, preferably, the electrochemical modification comprises the steps of: placing raw-material PAN-based carbon fibers in an electrolyte solution, and applying cyclic treatment between electrochemical oxidation and electrochemical reduction, to obtain the oxygen and nitrogen co-doped PAN-based carbon fibers.

The present invention also provides a method for preparing the oxygen and nitrogen co-doped PAN-based carbon fibers described above, the method comprising the steps of: placing raw-material PAN-based carbon fibers in an electrolyte solution, and applying cyclic treatment between electrochemical oxidation and electrochemical reduction, to obtain the oxygen and nitrogen co-doped PAN-based carbon fibers. In the preparation method, after the cyclic treatment between electrochemical oxidation and electrochemical reduction, an active layer formed by oxygen-containing active functional groups and nitrogen-containing active functional groups is obtained, wherein the nitrogen-containing active functional groups are obtained after activation of the non-active doped nitrogen inherent in the unmodified raw-material PAN-based carbon fibers by electrochemical modification.

In the preparation method above, preferably, based on the total mass of the oxygen and nitrogen co-doped PAN-based carbon fibers, the total quantity of electricity for electrochemical oxidation is 1,000 to 10,000 C/g, and the total quantity of electricity for electrochemical reduction is 1,000 to 10,000 C/g. During the cyclic treatment between electrochemical oxidation and electrochemical reduction, the electrochemical oxidation and the electrochemical reduction should be alternately performed, but which one of them is performed first or last is not limited. In addition, the number of cycles of electrochemical oxidation and electrochemical reduction is not limited, and when the total quantities of electricity for electrochemical oxidation and reduction meet the above requirements, the reactions can be stopped to obtain the oxygen and nitrogen co-doped PAN-based carbon fibers. If the total quantity of electricity for electrochemical oxidation and/or reduction is less than 1,000 C/g, the active layer will have insufficient active functional groups and low activity. If the total quantity of electricity for electrochemical oxidation and/or reduction is more than 10,000 C/g, the active layer will peel off, be damaged and loss the activity, even resulting in damaged substrate structure.

In the preparation method above, preferably, for the entire cyclic treatment, the total quantity of electricity for electrochemical oxidation is equal to or greater than the total quantity of electricity for electrochemical reduction. The quantity of electricity for electrochemical oxidation in each cycle and the quantity of electricity for electrochemical reduction in each cycle are not limited, and the former may be greater than, equal to, or smaller than the latter. Furthermore, the quantities of electricity for electrochemical oxidation in different cycles may be the same as or different from each other, and the quantities of electricity for electrochemical reduction in different cycles may be the same as or different from each other.

In the preparation method above, preferably, the electrolyte solution is an acidic electrolyte solution, a basic electrolyte solution, a neutral electrolyte solution, or the like.

In the preparation method above, preferably, the acidic electrolyte solution is one or a combination of more of aqueous solutions of oxygen-containing inorganic acids and the like. More preferably, the acidic electrolyte solution is an aqueous solution of sulfuric acid.

In the preparation method above, preferably, the basic electrolyte solution is one or a combination of more of aqueous solutions of an alkali metal hydroxide, an alkali earth metal hydroxide, an oxygen-containing salt of alkali metal, an ammonium salt and the like. More preferably, the basic electrolyte solution is an aqueous solution of ammonium bicarbonate.

In the preparation method above, preferably, the neutral electrolyte solution is one or a combination of more of aqueous solutions of sodium nitrate, potassium nitrate, ammonium nitrate, sodium sulfate, potassium sulfate, ammonium sulfate and the like. More preferably, the neutral electrolyte solution is an aqueous solution of sodium nitrate.

In the preparation method above, as long as the reactions can unimpededly proceed, a person skilled in the art may select and adjust the concentration and use amount of the above electrolyte solution as necessary. In addition, among the acidic electrolyte solution, the basic electrolyte solution and the neutral electrolyte solution described above, most preferred is an aqueous solution of sulfuric acid.

The oxygen and nitrogen co-doped PAN-based carbon fibers provided according to the present invention are prepared by electrochemical modification of raw-material PAN-based carbon fibers and have both oxygen-containing active functional groups and nitrogen-containing active functional groups formed at the edges of carbon basal planes of the fiber surface, such that the fibers have certain pseudocapacitive characteristics and electrocatalytic activity for oxygen reduction reactions and redox couples. Use of the oxygen and nitrogen co-doped PAN-based carbon fibers provided according to the present invention as electrode material can exploit either or both of the pseudocapacitive characteristics and the electrocatalytic activity to improve the activity and performance in use of electrode material, and offers advantages such as good activity, high conductivity, low material cost, stability, and a long lifetime. The method for preparing oxygen and nitrogen co-doped PAN-based carbon fibers by electrochemical modification provided according to the present invention has the advantages such as simple preparation, low production cost, and suitability for industrial production.

The oxygen and nitrogen co-doped PAN-based carbon fibers provided according to the present invention may be used for the manufacture of electrodes for cells utilizing oxygen dissolved in seawater, proton exchange membrane fuel cells, metal-air fuel cells, microbial fuel cells, a supercapacitor, redox flow cells, lead-acid cells, lithium-ion cells, electrochemical treatment of waste water, an electrochemical transducer, as well as for various technical fields of electrochemistry engineering using such electrode material.

DETAILED DESCRIPTION OF EMBODIMENTS

In order to provide a better understanding of the technical features, objectives and beneficial effects of the present invention, a detailed description of the technical solution of the present invention is provided below, but should not be construed as limiting the scope of embodiments of the present invention.

Figure 1:
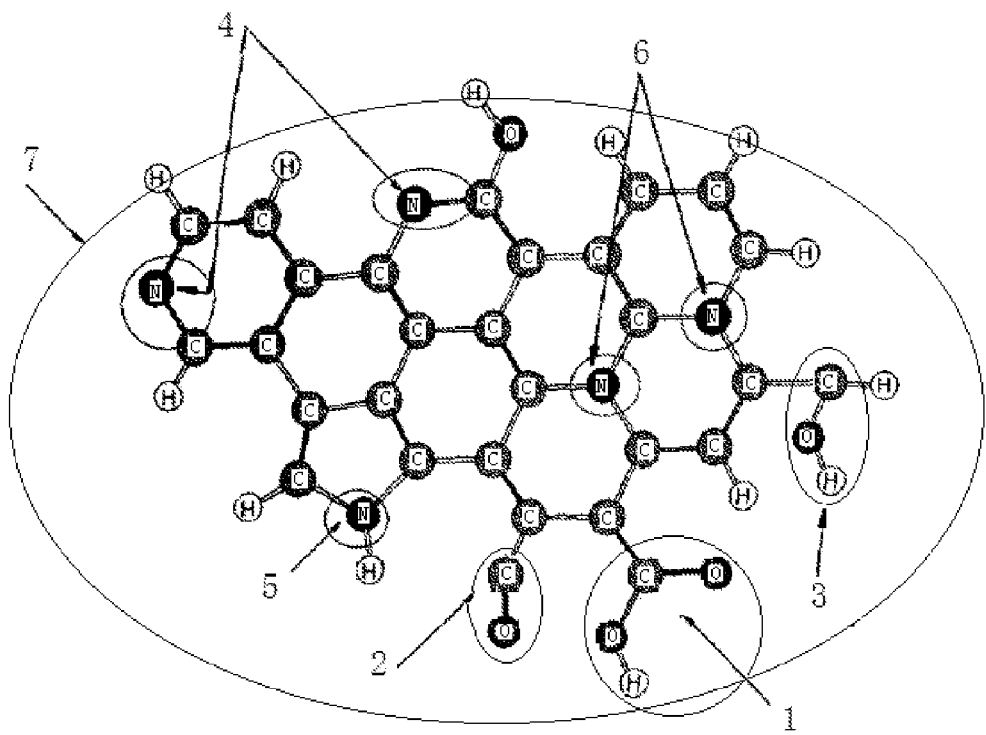
FIG. 1 is a schematic representation of structures of the active functional groups on the surface of the oxygen and nitrogen co-doped PAN-based carbon fibers provided according to the present invention.

FIG. 1 shows a schematic representation of the structures of the active functional groups on the surface of the oxygen and nitrogen co-doped PAN-based carbon fibers provided according to the present invention. On the surface of the oxygen and nitrogen co-doped PAN-based carbon fibers, there is an active layer 7 formed by carboxyl oxygen 1, ketonic oxygen 2, hydroxyl oxygen 3, pyridinic nitrogen 4, pyrrolic nitrogen 5 and graphitic nitrogen 6 at the edges of carbon basal planes, wherein the oxygen-containing active functional groups (carboxyl oxygen 1, ketonic oxygen 2, and hydroxyl oxygen 3), the nitrogen-containing active functional groups (pyridinic nitrogen 4, pyrrolic nitrogen 5 and graphitic nitrogen 6) and the active layer 7 formed thereby were obtained by electrochemical modification, and wherein the nitrogen-containing active functional groups (pyridinic nitrogen 4, pyrrolic nitrogen 5 and graphitic nitrogen 6) were obtained after activation of the non-active doped nitrogen inherent in the unmodified raw-material PAN-based carbon fibers by electrochemical modification.

Further descriptions of the technical solution of the present invention are provided below through examples.

Example 1

This example provides a kind of oxygen and nitrogen co-doped PAN-based carbon fiber filaments, which were prepared by electrochemical modification of the T700SC 12K PAN-based carbon fiber filaments such that their surface had an active layer formed by oxygen-containing active functional groups and nitrogen-containing active functional groups, wherein the nitrogen-containing active functional groups were obtained after activation of the non-active doped nitrogen inherent in the unmodified raw-material PAN-based carbon fibers by the electrochemical modification.

The method for preparing the oxygen and nitrogen co-doped PAN-based carbon fiber filaments according to this example comprised the steps of:
placing 1 g of T700SC 12K PAN-based carbon fiber filaments in a 0.5 M aqueous solution of sulfuric acid;
subjecting the raw-material PAN-based carbon fiber filaments to electrochemical anodic oxidation for 5 min and then to electrochemical cathodic reduction for 5 min, and further repeating this procedure 5 times, to obtain the oxygen and nitrogen co-doped PAN-based carbon fiber filaments;
wherein the total quantity of electricity supplied for the oxidation was 1,000 C (i.e. the total quantity of electricity for the 6 cycles of electrochemical oxidation), and the total quantity of electricity for the reduction was 1,000 C (i.e. the total quantity of electricity for the 6 cycles of electrochemical reduction).

Following the above preparation method expect for changing the total quantities of electricity supplied for oxidation and reduction, another three kinds of oxygen and nitrogen co-doped PAN-based carbon fiber filaments were correspondingly prepared, wherein the total quantities of electricity supplied for the oxidation/reduction in preparation of the three kinds of oxygen and nitrogen co-doped PAN-based carbon fiber filaments were 3,000 C/3,000 C; 6,000 C/6,000 C; and 10,000 C/0,000 C, respectively.

As a result, in this example totally four kinds of oxygen and nitrogen co-doped PAN-based carbon fiber filaments were prepared.

Figure 2:
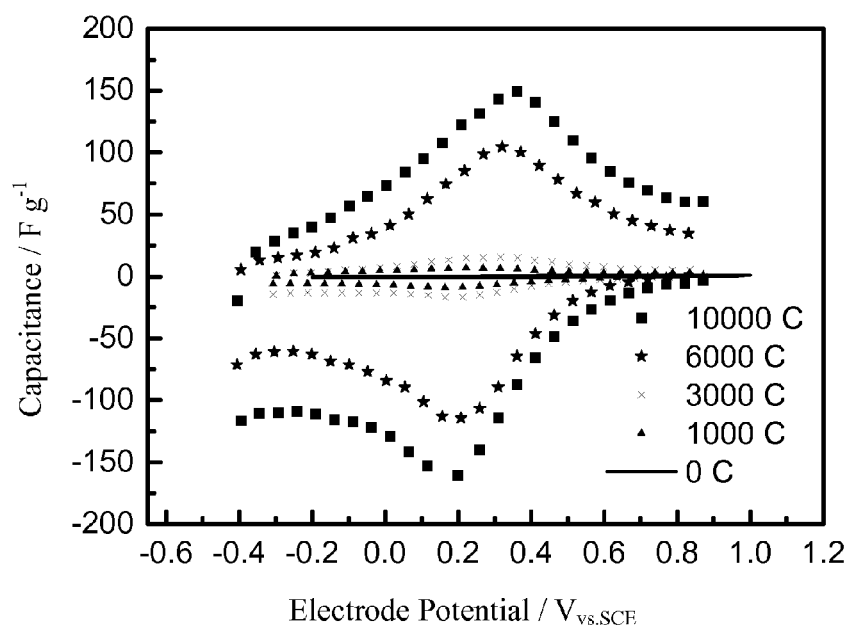
FIG. 2 shows the capacitance-electrode potential curves of cyclic voltammetry of four kinds of oxygen and nitrogen co-doped PAN-based carbon fiber filaments and the raw-material PAN-based carbon fiber filaments provided according to Example 1.

FIG. 2 shows the cyclic capacitance-electrode potential curves of cyclic voltammetry of the four kinds of oxygen and nitrogen co-doped PAN-based carbon fiber filaments and the raw-material PAN-based carbon fiber filaments provided according to this example in a 2 M solution of sulfuric acid. As shown in FIG. 2, the raw-material PAN-based carbon fiber filaments that were not electrochemically modified showed very small capacitance and no pseudocapacitive characteristics, whereas the electrochemically modified oxygen and nitrogen co-doped PAN-based carbon fiber filaments showed good symmetry and a pair of symmetric broadened redox peaks in their capacitance curves, corresponding to the consecutive redox reactions between the oxygen-containing active functional groups, i.e. the carboxyl oxygen, ketonic oxygen and hydroxyl oxygen. Therefore, the oxygen and nitrogen co-doped PAN-based carbon fiber filaments had reversible redox reactivity (pseudocapacitive characteristics), and their capacitance increased linearly with the increase in the quantity of the redox electricity supplied in the electrochemical modification. When both the total quantities of the electricity supplied for oxidation and reduction were 10,000 C, the specific capacitance of the product reached the maximal value 150 F/g (measured at a scanning speed of 5 mV/s). If the quantity of redox electricity supplied in the electrochemical modification was further increased, the active structure of the carbon fibers would be damaged, resulting in loss of activity.

Figure 3:
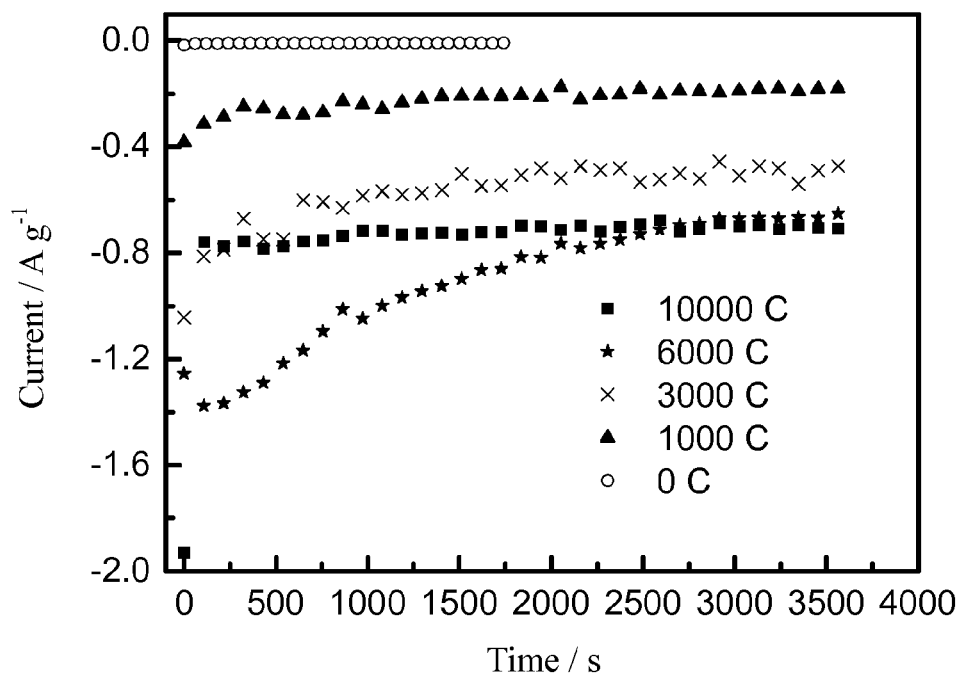
FIG. 3 shows the chronoamperometric plots of four kinds of oxygen and nitrogen co-doped PAN-based carbon fiber filaments and the raw-material PAN-based carbon fiber filaments provided according to Example 1.

FIG. 3 shows the chronoamperometric plots of the four kinds of oxygen and nitrogen co-doped PAN-based carbon fiber filaments and the raw-material PAN-based carbon fiber filaments provided according to this example in natural seawater at a flow rate of 3.2 cm/s under a potential of $-0.4$ $V_{vs.SCE}$. As shown in FIG. 3, the raw-material PAN-based carbon fiber filaments that were not electrochemically modified showed no electrocatalytic activity for the cathodic reduction of the oxygen dissolved in seawater, and the ORR current was only about 6 mA/g. In contrast, the electrochemically modified oxygen and nitrogen co-doped PAN-based carbon fiber filaments showed significantly increased ORR current, which could be up to 700 mA/g at a seawater flow rate of 3.2 cm/s, because one or more of the nitrogen-containing active functional groups (i.e. the pyridinic nitrogen, pyrrolic nitrogen and graphitic nitrogen) at the edges of carbon basal planes on the surface of the carbon fibers had electrocatalytic activity for cathodic oxygen reduction; and the ORR current also increased with the increase in the quantity of the redox electricity supplied in the electrochemical modification. After both the total quantities of electricity supplied for oxidation and reduction reached 6,000 C, the ORR current no longer increased and was substantially stable. If the quantity of redox electricity supplied in the electrochemical modification exceeded 10,000 C, the active structure of the carbon fibers would be damaged, resulting in loss of activity.

Figure 4:
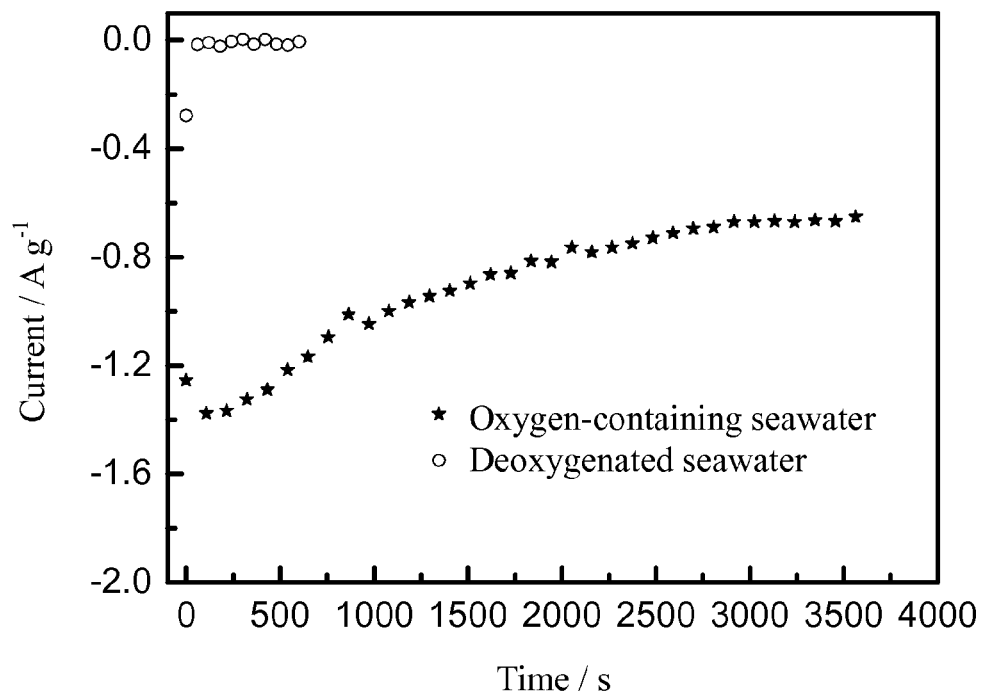
FIG. 4 shows the chronoamperometric plots of one kind of oxygen and nitrogen co-doped PAN-based carbon fiber filaments provided according to Example 1 in oxygen-containing seawater and deoxygenated seawater.

FIG. 4 shows the chronoamperometric plots of the oxygen and nitrogen co-doped PAN-based carbon fiber filaments prepared with both the total quantities of electricity supplied for oxidation and reduction being 6,000 C according to this example in oxygen-containing seawater and deoxygenated seawater at a flow rate of 3.2 cm/s under a potential of $-0.4$ $V_{vs.SCE}$. As shown in FIG. 4, after removal of the dissolved oxygen from seawater, the ORR current decreased to nearly zero, which further demonstrates that the oxygen and nitrogen co-doped PAN-based carbon fiber filaments prepared by electrochemical modification according to the present invention have electrocatalytic activity for the cathodic oxygen reduction reaction.

Figure 5A:
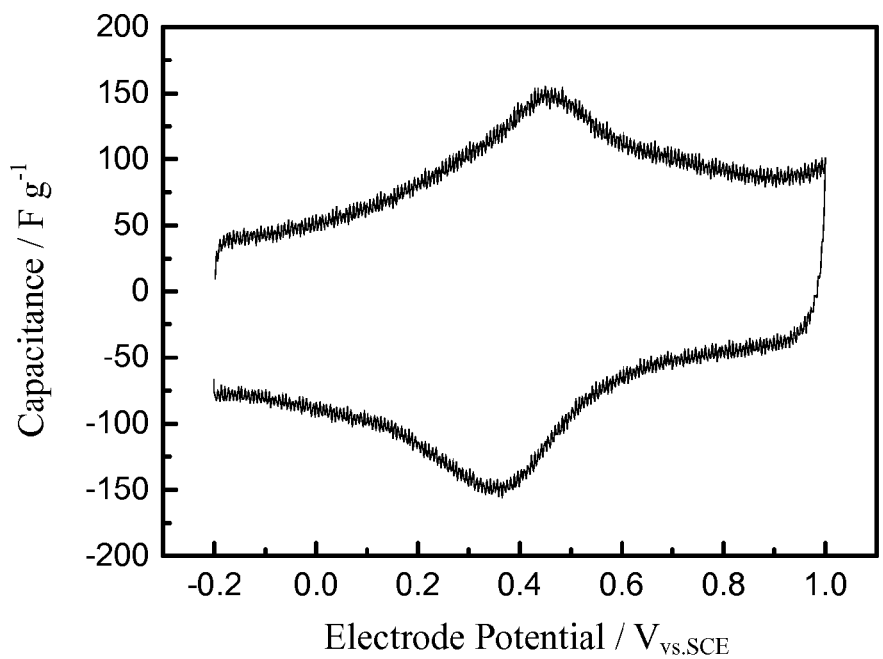
FIG. 5a shows the capacitance-electrode potential curve of cyclic voltammetry of electrochemically modified graphite fiber filaments.
Figure 5B:
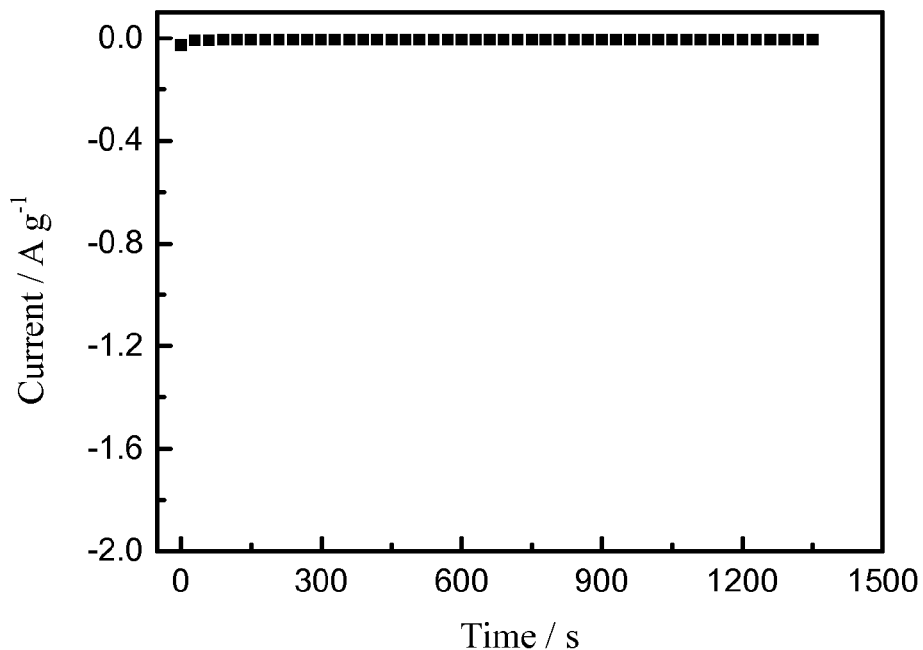
FIG. 5b shows the chronoamperometric plot of electrochemically modified graphite fiber filaments.

1 g of the raw-material PAN-based carbon fiber filaments were graphitized at a high temperature of 2,200° C. to 3,000° C. to afford graphite fiber filaments, which were then subjected to electrochemical modification with both the total quantities of electricity supplied for oxidation and reduction being 6,000 C according to the preparation method of this example, to afford electrochemically modified graphite fiber filaments. The electrochemically modified graphite fiber filaments were assayed according to the assay conditions shown in FIG. 2 and FIG. 3 for a cyclic capacitance-electrode potential curve of cyclic voltammetry and a chronoamperometric plot, and the results are shown in FIG. 5a and FIG. 5b. FIG. 5a shows the cyclic capacitance-electrode potential curve of cyclic voltammetry of the electrochemically modified graphite fiber filaments in a 2 M solution of sulfuric acid, demonstrating that the electrochemically modified graphite fiber filaments have pseudocapacitive characteristics. FIG. 5b shows the chronoamperometric plot of the electrochemically modified graphite fiber filaments in seawater at a flow rate of 3.2 cm/s under a potential of $-0.4$ $V_{vs.SCE}$, demonstrating that the electrochemically modified graphite fiber filaments have no electrocatalytic activity for the cathodic oxygen reduction reaction. That is because the graphite fiber filaments obtained after high-temperature graphitization of the raw-material PAN-based carbon fiber filaments did not have doped nitrogen any more, and accordingly the electrochemical modification thereof merely resulted in graphite fiber filaments having oxygen-containing active functional groups only.

Table 1 shows the XPS analysis results of the surface elements of the four kinds of oxygen and nitrogen co-doped PAN-based carbon fiber filaments and the raw-material PAN-based carbon fiber filaments provided according to this example. As shown in Table 1, the raw-material PAN-based carbon fiber filaments that were not electrochemically modified had doped nitrogen on the surface, while the oxygen and nitrogen co-doped PAN-based carbon fiber filaments that were electrochemically modified showed a significant increase in surface oxygen content, which was responsible for their pseudocapacitive characteristics, but also showed a little change in nitrogen content. Considering the above electrochemical assay results and the fact that there was no nitrogen-containing compound in the treatment solution, it can be inferred that the non-active doped nitrogen inherent in the raw-material PAN-based carbon fibers were activated by the electrochemical modification and converted into nitrogen-containing active functional groups.

TABLE 1

| | Sample | | | | |
|---|---|---|---|---|---|
| atom % | 0 C | 1000 C | 3000 C | 6000 C | 10000 C |
| C | 95.5 | 81.7 | 80.0 | 76.8 | 74.5 |
| O | 2.5 | 15.7 | 17.3 | 20.3 | 22.7 |
| N | 2.0 | 2.6 | 2.7 | 2.9 | 2.8 |

Example 2

This example provides a kind of oxygen and nitrogen co-doped PAN-based carbon fiber felt, which was prepared by electrochemical modification of PAN-based carbon fiber felt (thickness: 6 mm; mass per geometric area: 0.1 g/cm$^2$) such that its surface had an active layer formed by oxygen-containing active functional groups and nitrogen-containing active functional groups, wherein the nitrogen-containing active functional groups were obtained after activation of the non-active doped nitrogen inherent in the unmodified raw-material PAN-based carbon fibers by the electrochemical modification.

The method for preparing the oxygen and nitrogen co-doped PAN-based carbon fiber felt according to this example comprised the steps of:
placing 0.1 g of the PAN-based carbon fiber felt in a 10 wt % aqueous solution of ammonium bicarbonate;
subjecting the raw-material PAN-based carbon fiber felt to electrochemical anodic oxidation for 5 min and then to electrochemical cathodic reduction for 2 min, and further repeating this procedure 4 times, wherein the total quantity of electricity supplied for the oxidation was 5,000 C/g (i.e. the total quantity of electricity for the 5 cycles of electrochemical oxidation) and the total quantity of electricity for the reduction was 2,000 C/g (i.e. the total quantity of electricity for the 5 cycles of electrochemical reduction), so as to obtain the oxygen and nitrogen co-doped PAN-based carbon fiber felt.

Figure 6A:
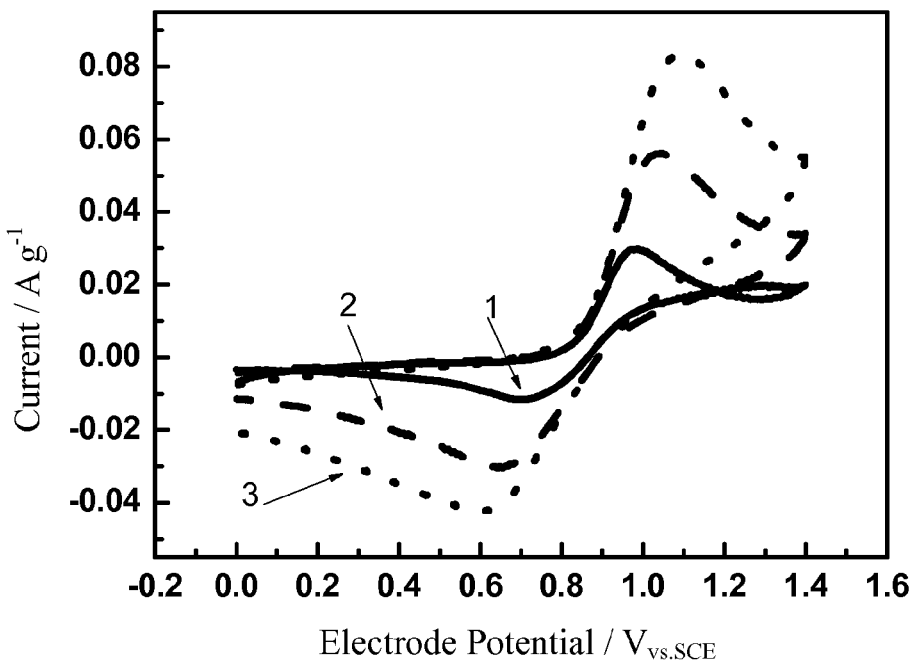
FIG. 6a shows the cyclic voltammetry curves of the raw-material PAN-based carbon fiber felt according to Example 2.
Figure 6B:
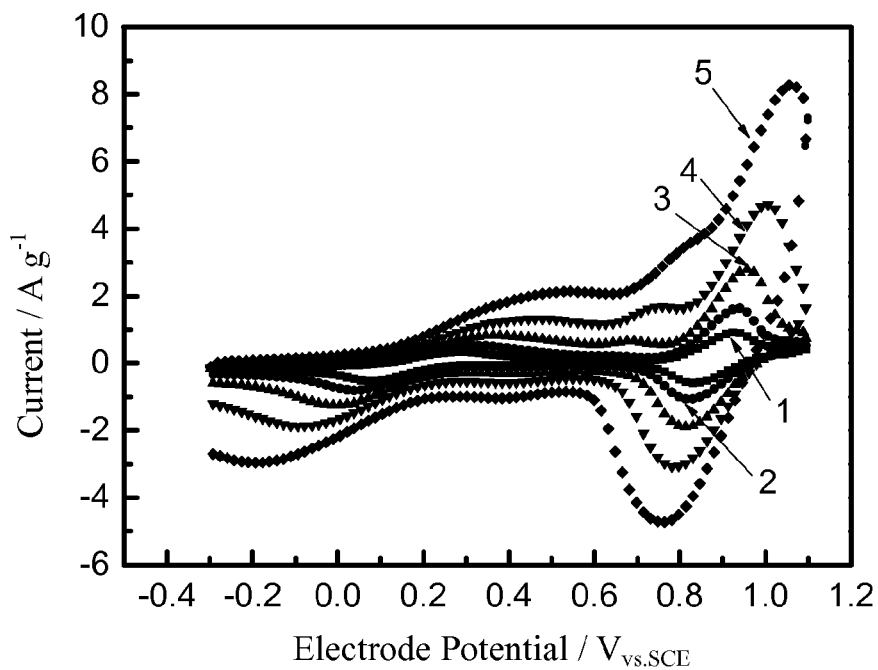
FIG. 6b shows the cyclic voltammetry curves of the oxygen and nitrogen co-doped PAN-based carbon fiber felt according to Example 2.

FIG. 6a shows the cyclic voltammetry curves of the raw-material PAN-based carbon fiber felt according to this example in an aqueous solution of vanadyl sulfate and sulfuric acid (1 M $VOSO_4$+2 M $H_2SO_4$). Curves 1-3 in FIG. 6a correspond to the scanning speeds of 5, 10 and 20 mV/s, respectively. FIG. 6b shows the cyclic voltammetry curves of the oxygen and nitrogen co-doped PAN-based carbon fiber felt according to this example in an aqueous solution of vanadyl sulfate and sulfuric acid (1 M $VOSO_4$+2 M $H_2SO_4$). Curves 1-5 in FIG. 6b correspond to the scanning speeds of 1.5, 3, 6, 12 and 25 mV/s, respectively. Upon a comparative analysis of FIG. 6a and FIG. 6b, it can be seen that, the raw-material PAN-based carbon fiber felt that was not electrochemically modified showed larger difference in peak potential between the oxidation and reduction peaks of $V^{4+}/V^{5+}$ and lower current intensity at the peaks, than those of the electrochemically modified oxygen and nitrogen co-doped PAN-based carbon fiber felt. This indicates that the electrochemically modified oxygen and nitrogen co-doped PAN-based carbon fiber felt had better reversible electrocatalytic activity for the redox reactions of the $V^{4+}/V^{5+}$ couple.

Example 3

This example provides a kind of oxygen and nitrogen co-doped PAN-based carbon fiber filaments, which were prepared by electrochemical modification of the T300 12K PAN-based carbon fiber filaments such that their surface had an active layer formed by oxygen-containing active functional groups and nitrogen-containing active functional groups, wherein the nitrogen-containing active functional groups were obtained after activation of the non-active doped nitrogen inherent in the unmodified raw-material PAN-based carbon fibers by the electrochemical modification. This example further provides a brush electrode made from the oxygen and nitrogen co-doped PAN-based carbon fiber filaments, which can be used for the waste water treatment technology by the Electro-Fenton method.

The method for preparing the oxygen and nitrogen co-doped PAN-based carbon fiber filaments and the brush electrode made thereof according to this example comprised the steps of:
placing 2 g of T300 12K PAN-based carbon fiber filaments in a 10 wt % aqueous solution of sodium nitrate;
subjecting the raw-material PAN-based carbon fiber filaments to electrochemical cathodic reduction for 3 min and then to electrochemical anodic oxidation for 5 min, and further repeating this procedure 3 times, wherein the total quantity of electricity supplied for the oxidation was 5,000 C/g (i.e. the total quantity of electricity for the 4 cycles of electrochemical oxidation) and the total quantity of electricity for the reduction was 4,000 C/g (i.e. the total quantity of electricity for the 4 cycles of electrochemical reduction), so as to obtain the oxygen and nitrogen co-doped PAN-based carbon fiber filaments.

A brush electrode was made from the oxygen and nitrogen co-doped PAN-based carbon fiber filaments and titanium wire having a diameter of 1 mm, wherein the brush body was 180 mm long and had a diameter of 30 mm.

Figure 7A:
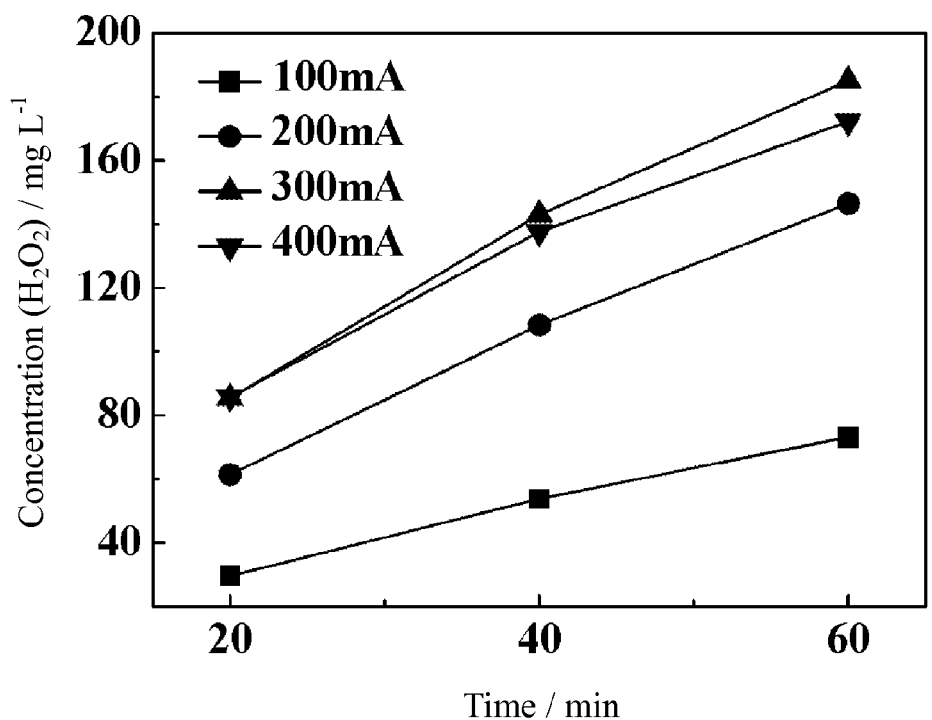
FIG. 7a shows the $H_2O_2$-production curves of the brush electrode made from the oxygen and nitrogen co-doped PAN-based carbon fiber filaments according to Example 3.
Figure 7B:
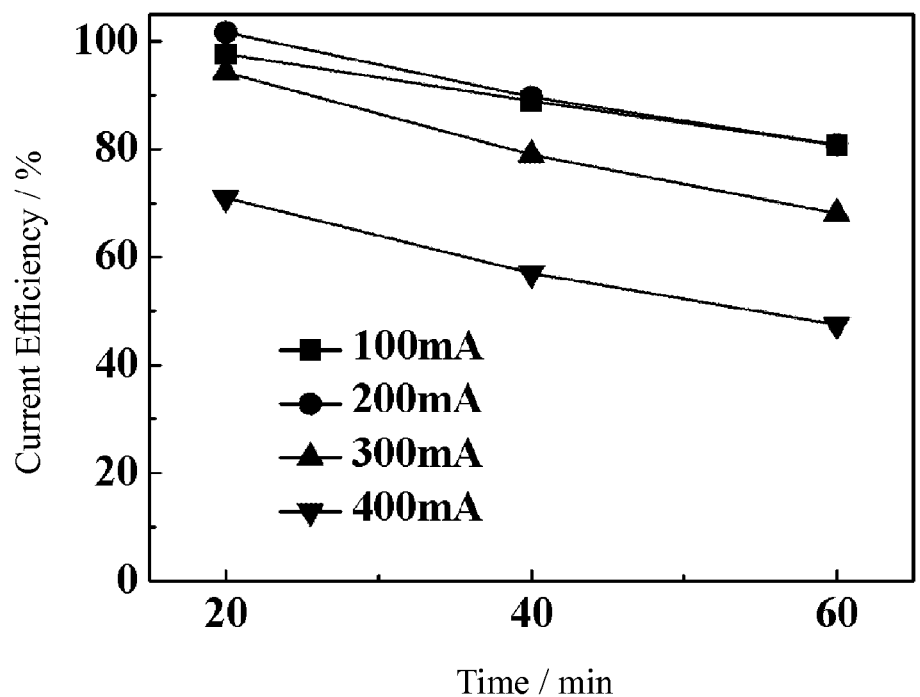
FIG. 7b shows the current efficiency curves of the brush electrode made from the oxygen and nitrogen co-doped PAN-based carbon fiber filaments according to Example 3.

FIG. 7a shows the $H_2O_2$-production curves of the brush electrode made from the oxygen and nitrogen co-doped PAN-based carbon fiber filaments according to this example in a 0.4 M solution of $Na_2SO_4$ under different currents; FIG. 7b shows the current efficiency curves of the brush electrode made from the oxygen and nitrogen co-doped PAN-based carbon fiber filaments according to this example in a 0.4 M solution of $Na_2SO_4$ under different currents. As shown in FIG. 7a, when the current intensity was 100-300 mA, the $H_2O_2$ concentration increased with the increase in current intensity; when the current intensity was 300 mA, the $H_2O_2$ concentration could reach 185 mg/L upon 1 h reaction; and when the current intensity was 400 mA, the $H_2O_2$ concentration was lower than that at 300 mA. As shown in FIG. 7b, when the current intensity was 100-300 mA, the current efficiency at the initial stage of reaction was close to 100%; with the lapse of the reaction time, the current efficiency gradually decreased, but were above 65% upon 1 h reaction; and when the current intensity was 400 mA, side reactions increased, resulting in considerably decreased current efficiency as compared to that at 300 mA.

The brush electrode according to this example was used to treat waste water containing 20 mg/L methylene blue by the Electro-Fenton method, in which the initial pH of the waste water was adjusted to 3, the decoloration was 91% upon 5-min electrolysis, and the decoloration was 98% or more after 30 min. This result demonstrates that the electrochemically modified PAN-based carbon fiber filaments and the brush electrode made thereof can serve as the highly efficient cathode material and electrode for the Electro-Fenton method.

Example 4

This example provides an oxygen and nitrogen co-doped PAN-based carbon-fiber brush, which was prepared by making a brush body from the T300 12K PAN-based carbon fiber filaments and then electrochemically modifying the brush body, such that the surface of carbon fibers in the brush body had an active layer formed by oxygen-containing active functional groups and nitrogen-containing active functional groups, wherein the nitrogen-containing active functional groups were obtained after activation of the non-active doped nitrogen inherent in the unmodified raw-material PAN-based carbon fibers by the electrochemical modification. The oxygen and nitrogen co-doped PAN-based carbon-fiber brush can be used as the positive electrode in seawater cells utilizing the dissolved oxygen.

The method for preparing the oxygen and nitrogen co-doped PAN-based carbon-fiber brush according to this example comprised the steps of:
making a brush body from the oxygen and nitrogen co-doped PAN-based carbon fiber filaments and titanium wire having a diameter of 1 mm, wherein the brush body was 180 mm long and had a diameter of 30 mm;

then placing the carbon-fiber brush in a 2M aqueous solution of sulfuric acid; and subjecting the carbon-fiber brush to electrochemical anodic oxidation for 4 min and then to electrochemical cathodic reduction for 3 min, and further repeating this procedure 6 times, wherein the total quantity of electricity supplied for the oxidation was 9,000 C/g (i.e. the total quantity of electricity for the 7 cycles of electrochemical oxidation) and the total quantity of electricity for the reduction was 6,000 C/g (i.e. the total quantity of electricity for the 7 cycles of electrochemical reduction), so as to obtain the oxygen and nitrogen co-doped PAN-based carbon-fiber brush.

The effect of the flow rate of natural seawater on the cathodic oxygen reduction reaction was measured with the above oxygen and nitrogen co-doped PAN-based carbon-fiber brush, and the results are shown in Table 2 and Table 3. Table 2 shows the initial reduction potentials of oxygen when using electrochemically unmodified and modified PAN-based carbon-fiber brushes in seawater at different flow rates; and Table 3 shows the cathodic oxygen reduction currents at corresponding polarization potentials when using the electrochemically unmodified and modified PAN-based carbon-fiber brushes in seawater at different flow rates. As shown in Table 2 and Table 3, when compared to the electrochemically unmodified PAN-based carbon-fiber brush, the electrochemically modified PAN-based carbon-fiber brush showed a nearly 300 mV higher initial reduction potential of oxygen, and higher working current under the same cathodic polarization potential. Furthermore, the higher the flow rate, the higher the oxygen reduction current was. These results demonstrate that the oxygen and nitrogen co-doped PAN-based carbon-fiber brush obtained by electrochemical modification showed very high electro-reducing activity for the oxygen dissolved in seawater.

A seawater cell utilizing the oxygen dissolved in seawater can be manufactured by using the oxygen and nitrogen co-doped PAN-based carbon-fiber brush of this example as the positive electrode. This cell was constituted with (i) a central magnesium anode bar as the negative electrode, and (ii) totally 60 oxygen and nitrogen co-doped carbon-fiber brushes arranged in an upper layer and a lower layer around the magnesium bar, as the positive electrode. The positive electrode was fixed to a full-titanium metal frame by welding, the negative electrode was fixed at the center of the frame with a bolt in an insulating jacket, the frame was 360 mm×360 mm×390 mm in size (the volume of the cell was about 50 L), and the initial distance between the positive and negative electrodes was 50 mm. As a result, the cell had a maximal power of 5.4 W, a minimal power of 2 W, and a volumetric specific power of 40 W/m$^3$, demonstrating that the cell had better performance than SWB1200 whose volumetric specific power is 2.7 W/m$^3$. Therefore, since the seawater cell utilizing the oxygen dissolved in seawater employed the oxygen and nitrogen co-doped PAN-based carbon-fiber brush of this example as the positive electrode, the seawater cell had a smaller volume and a higher volumetric specific power than those in the prior art.

The invention claimed is:

1. An oxygen and nitrogen co-doped polyacrylonitrile-based carbon fiber, prepared by electrochemical modification of a raw-material polyacrylonitrile-based carbon fiber such that its surface has an active layer formed by oxygen-containing active functional groups and nitrogen-containing active functional groups, wherein the nitrogen-containing active functional groups are obtained by activation of the doped nitrogen inherent in the raw-material polyacrylonitrile-based carbon fiber by the electrochemical modification, wherein the nitrogen-containing active functional groups comprise 2-pyridone and/or 2-hydroxyl pyridine, wherein the oxygen-containing active functional groups have reversible redox reactivity, and wherein the nitrogen-containing active functional groups have electrocatalytic activity for cathodic oxygen reduction, wherein the electrochemical modification comprises the steps of:

placing a raw-material polyacrylonitrile-based carbon fiber in an electrolyte solution, and applying cyclic treatment between electrochemical oxidation and electrochemical reduction, to obtain the oxygen and nitrogen co-doped polyacrylonitrile-based carbon fiber.

2. The oxygen and nitrogen co-doped polyacrylonitrile-based carbon fiber according to claim 1, wherein the nitrogen-containing active functional groups further comprise functional groups selected from the group consisting of one or a combination of more than one of pyridinic nitrogen

TABLE 2

| Tangent plane flow rate/cm · s$^{-1}$ | Initial reduction potential of oxygen | |
| --- | --- | --- |
| | $E_{unmodified}$/mV$_{vs.SCE}$ | $E_{modified}$/mV$_{vs.SCE}$ |
| 1.22 | −328 | −47 |
| 3.44 | −335 | −47 |
| 5.34 | −350 | −47 |
| 5.59 | −378 | −45 |
| 5.90 | −345 | −47 |
| 6.92 | −353 | −45 |
| 7.23 | −395 | −47 |
| 9.25 | −400 | −47 |

TABLE 3

| Tangent plane flow rate/cm · s$^{-1}$ | E = −200 mV$_{vs.SCE}$ | | E = −300 mV$_{vs.SCE}$ | | E = −700 mV$_{vs.SCE}$ | |
| --- | --- | --- | --- | --- | --- | --- |
| | $I_{modified}$/mA | $I_{unmodified}$/mA | $I_{modified}$/mA | $I_{unmodified}$/mA | $I_{modified}$/mA | $I_{unmodified}$/mA |
| 1.22 | −37.6 | −0.103 | −80.5 | −0.546 | −140.6 | −31.4 |
| 3.44 | −45.2 | −0.224 | −100.5 | −0.866 | −275 | −51.1 |
| 5.34 | −55.4 | −0.301 | −118.7 | −1.038 | −352 | −56.5 |
| 5.59 | −56.0 | −0.325 | −131.8 | −1.142 | −361 | −60.2 |
| 5.90 | −54.6 | −0.352 | −136.6 | −1.205 | −419 | −63.5 |
| 6.92 | −59.1 | −0.41 | −143.2 | −1.314 | −483 | −68.6 |
| 7.23 | −60.8 | −0.41 | −158 | −1.366 | −515 | −74.2 |
| 9.25 | −63.8 | −0.702 | −160 | −1.794 | −556 | −89.1 | except for 2-hydroxyl pyridine, derivatives of pryidinone except for 2-pyridone, pyrrolic nitrogen, and graphitic nitrogen located at the edges of carbon basal planes on the surface of the oxygen and nitrogen co-doped polyacrylonitrile-based carbon fiber.

3. The oxygen and nitrogen co-doped polyacrylonitrile-based carbon fiber according to claim 1, wherein the oxygen-containing active functional groups are selected from the group consisting of one or a combination of more than one of carboxyl oxygen, ketonic oxygen, and hydroxyl oxygen located at the edges of carbon basal planes on the surface of the oxygen and nitrogen co-doped polyacrylonitrile-based carbon fiber.

4. The oxygen and nitrogen co-doped polyacrylonitrile-based carbon fiber according to claim 1, wherein the raw-material polyacrylonitrile-based carbon fiber has not been treated by graphitization, and has a nitrogen content of 1% or more with respect to the total mass of the raw-material polyacrylonitrile-based carbon fiber.

5. The oxygen and nitrogen co-doped polyacrylonitrile-based carbon fiber of claim 1, wherein the carbon fiber has a shape selected from the group consisting of one or a combination of more than one of the shapes of a bundle, felt, foam, a brush, paper and cloth.

6. A method for preparing the oxygen and nitrogen co-doped polyacrylonitrile-based carbon fiber of claim 1, comprising the steps of:
   placing a raw-material polyacrylonitrile-based carbon fiber in an electrolyte solution, and
   applying cyclic treatment between electrochemical oxidation and electrochemical reduction, to obtain the oxygen and nitrogen co-doped polyacrylonitrile-based carbon fiber,
   wherein the total quantity of electricity for electrochemical oxidation is 1,000 to 10,000 Coulombs/g, and the total quantity of electricity for electrochemical reduction is 1,000 to 10,000 Coulombs/g, based on the mass of the raw material polyacrylonitrile-based carbon fiber.

7. The method according to claim 6, wherein the total quantity of electricity for electrochemical oxidation is equal to or greater than the total quantity of electricity for electrochemical reduction.

8. The method according to claim 6, wherein the electrolyte solution is an acidic electrolyte solution, a basic electrolyte solution, or a neutral electrolyte solution.

9. The method according to claim 8, wherein the acidic electrolyte solution is one or a combination of more than one aqueous solution of oxygen-containing inorganic acids.

10. The method according to claim 9, wherein the acidic electrolyte solution is an aqueous solution of sulfuric acid.

11. The method according to claim 8, wherein the basic electrolyte solution is selected from the group consisting of one or a combination of more than one aqueous solution of an alkali metal hydroxide, an alkali earth metal hydroxide, an oxygen-containing salt of alkali metal, and an ammonium salt.

12. The method according to claim 11, wherein the basic electrolyte solution is an aqueous solution of ammonium bicarbonate.

13. The method according to claim 8, wherein the neutral electrolyte solution is one or a combination of more than one aqueous solution of sodium nitrate, potassium nitrate, ammonium nitrate, sodium sulfate, potassium sulfate, and ammonium sulfate.

14. The method according to claim 13, wherein the neutral electrolyte solution is an aqueous solution of sodium nitrate.

* * * * *